(12) United States Patent
Bublewitz et al.

(10) Patent No.: US 8,978,930 B2
(45) Date of Patent: Mar. 17, 2015

(54) CONTAINER

(75) Inventors: Alexander Bublewitz, Herborn (DE); Matthias Suchan, Hachenburg (DE)

(73) Assignee: Kettenbach GmbH & Co. KG, Eschenburg (DE)

( * ) Notice: Subject to any disclaimer, the term of this patent is extended or adjusted under 35 U.S.C. 154(b) by 508 days.

(21) Appl. No.: 12/678,985

(22) PCT Filed: Sep. 17, 2008

(86) PCT No.: PCT/EP2008/007769
§ 371 (c)(1),
(2), (4) Date: Jun. 18, 2010

(87) PCT Pub. No.: WO2009/036963
PCT Pub. Date: Mar. 26, 2009

(65) Prior Publication Data
US 2011/0056985 A1    Mar. 10, 2011

(30) Foreign Application Priority Data

Sep. 19, 2007  (DE) .......................... 10 2007 044 983
Jun. 11, 2008  (DE) .......................... 20 2008 007 801

(51) Int. Cl.
*B67D 7/70* (2010.01)
*B67D 7/78* (2010.01)
*B67D 7/22* (2010.01)
(Continued)

(52) U.S. Cl.
CPC ........... *B05C 17/00553* (2013.01); *A61C 5/068* (2013.01); *B05C 17/00559* (2013.01); *B05C 17/00563* (2013.01); *B05C 17/00576* (2013.01); *B05C 17/00579* (2013.01); *B05C 17/00593* (2013.01); *B05C 17/01* (2013.01); *A61C 5/062* (2013.01); *B05C 17/00506* (2013.01); *B05C 17/00516* (2013.01)
USPC ........................... 222/145.6; 222/137; 222/47

(58) Field of Classification Search
USPC ............... 222/137, 145.5, 145.6, 41, 47, 156; 433/89, 90
See application file for complete search history.

(56) References Cited

U.S. PATENT DOCUMENTS 3,738,535 A * 6/1973 Nicholls ........................ 222/137
4,538,920 A * 9/1985 Drake ........................ 366/181.5
(Continued)

FOREIGN PATENT DOCUMENTS

DE         93 04 337 U1    3/1993
DE        297 09 383 U1    5/1997
(Continued)

OTHER PUBLICATIONS

European Patent Office Communication of a Notice of Opposition dated Dec. 10, 2012 for Application No. 08802294.2-2424 / 2190592.

*Primary Examiner* — Paul R Durand
*Assistant Examiner* — Matthew Lembo
(74) *Attorney, Agent, or Firm* — McDonnell Boehnen Hulbert & Berghoff LLP (57) ABSTRACT

The invention relates to a container (1) for storing and discharging at least two components, in particular by means of a discharge gun or the like. The container (1) has at least two chambers (4a, 4b) for accommodating the components, a plunger means (15, 18, 20) for simultaneously discharging the components from the chambers, a sealing means for sealing the chambers, which sealing means can be opened and a mixer (8).

16 Claims, 9 Drawing Sheets

(51) Int. Cl.
  *B05C 17/005* (2006.01)
  *A61C 5/06* (2006.01)
  *B05C 17/01* (2006.01)

(56) References Cited

U.S. PATENT DOCUMENTS

| | | | | |
|---|---|---|---|---|
| 4,690,306 | A | * | 9/1987 | Staheli .................. 222/80 |
| 4,915,695 | A | * | 4/1990 | Koobs ................... 604/191 |
| 5,052,927 | A | | 10/1991 | Discko, Jr. |
| 5,065,906 | A | | 11/1991 | Maeder |
| 5,114,240 | A | * | 5/1992 | Kindt-Larsen et al. ....... 366/129 |
| 5,333,760 | A | * | 8/1994 | Simmen .................. 222/137 |
| 5,443,183 | A | * | 8/1995 | Jacobsen et al. .......... 222/145.6 |
| 5,878,922 | A | * | 3/1999 | Boring ................... 222/387 |
| 6,065,645 | A | * | 5/2000 | Sawhney et al. .......... 222/137 |
| 6,458,095 | B1 | * | 10/2002 | Wirt et al. ............... 604/82 |
| 6,598,766 | B1 | * | 7/2003 | Brugner ................. 222/326 |
| 7,497,355 | B2 | * | 3/2009 | Horner et al. ............ 222/137 |
| 7,882,983 | B2 | | 2/2011 | Beidt et al. |
| 7,963,937 | B2 | * | 6/2011 | Pauser et al. ............. 604/82 |
| 7,997,450 | B2 | * | 8/2011 | Heusser et al. .......... 222/145.6 |
| 8,033,429 | B2 | * | 10/2011 | Keller .................. 222/145.6 |
| 2006/0157508 | A1 | | 7/2006 | Suchan et al. |
| 2007/0023450 | A1 | * | 2/2007 | Horth et al. ............. 222/137 |
| 2007/0051750 | A1 | | 3/2007 | Suchan et al. |
| 2007/0090079 | A1 | | 4/2007 | Kelller |
| 2007/0166660 | A1 | | 7/2007 | Peuker et al. |
| 2007/0175921 | A1 | | 8/2007 | Keller |
| 2007/0228076 | A1 | * | 10/2007 | Horner et al. ............ 222/135 |

FOREIGN PATENT DOCUMENTS

| | | | |
|---|---|---|---|
| DE | 199 61 485 | A1 | 7/2001 |
| DE | 101 40 650 | A1 | 8/2001 |
| DE | 103 37 789 | A1 | 9/2005 |
| DE | 10 2005 002 850 | A1 | 8/2006 |
| EP | 0 624 403 | B1 | 8/1997 |
| EP | 1 256 389 | A2 | 11/2002 |
| EP | 1389448 | A1 | 2/2004 |
| EP | 1 426 017 | A2 | 9/2004 |
| EP | 1 679 126 | A1 | 12/2006 |
| GB | 2082686 | A * | 3/1982 |
| GB | 2 276 365 | A | 9/1994 |
| GB | 2 434 136 | A | 7/2007 |
| WO | 0230314 | A1 | 4/2002 |
| WO | 03041605 | A1 | 5/2003 |
| WO | 2005/016170 | A2 | 2/2005 |
| WO | 2005/016783 | A1 | 2/2005 |
| WO | 2005118154 | A1 | 12/2005 |
| WO | WO 2005118154 | A1 * | 12/2005 |
| WO | 2006/005213 | A1 | 1/2006 |
| WO | 2006132932 | A1 | 12/2006 |
| WO | 2007047381 | A1 | 4/2007 |
| WO | 2007104037 | A2 | 9/2007 |
| WO | 2007126532 | A2 | 11/2007 |

* cited by examiner

CONTAINER

The invention relates to a container for storing and discharging at least two components, in particular by means of a discharge gun or the like. The container has at least two chambers for accommodating the components, a plunger means for simultaneously discharging the components from the chambers and a sealing means for sealing the chambers, which sealing means can be opened.

A container of this type in the form of a double syringe is known from WO 2005/016170 A2. A similar container is also disclosed in EP 1 426 017 A2. These containers are fitted with a plunger of a plunger rod associated with the latter for each chamber in which the components are accommodated, which plunger projects from the back of the container. This brings with it the risk of the containers being opened and emptied by inadvertent pushing forward of the plunger rods in the event of improper handling during transportation or storage. The handling of the various plunger rods is sometimes found to be awkward. Furthermore, a mixer or similar applicator must sometimes be put on and/or the container must be opened in a plurality of separate work steps.

Containers for storing and discharging two components in which a plunger rod is provided which projects from the back of the container are also in each case known from EP 1 679 126 A1 and EP 0 624 403 B1. With these containers, a user must likewise first fix a mixer or applicator to the container after opening the container before the components accommodated therein can be dispensed.

Furthermore, a container is offered by TAH Industries, Inc., Robbinsville, USA under the name 'u-TAH™ nano', which has two chambers which are arranged coaxially with respect to one another and essentially behind one another and which can be emptied by means of a pot-like transfer plunger. This container is supplied with a closure cap which must be removed before the first use in order, if appropriate, to fix a separate mixer or similar applicator to the container. The 'u-TAH™ nano' container has a retaining section which is suitable for connecting to a discharge gun which is sold under the name 'Centrix®' by Centrix, Inc., Shelton, USA. A gun of this type is also described in EP 1 256 389 A2.

Discharge guns of this type are present in almost every dental practice as manual dispensers for what are known as preloaded tips (PLTs) for discharging 1 component dental composites. From an economic viewpoint, it is therefore desirable to use these existing dispensers or guns for as many dental material groups as possible and in particular also for 2 component systems.

It is an object of the present invention to provide a container of the type mentioned in the introduction, which enables a high degree of user-friendliness while at the same time enabling secure storage of the components.

This object is essentially achieved with a container with the features of claim 1. The invention stands out in particular on account of the combination of a container with a mixer which is pre-installed in the delivery state, a sealing means which can be opened without uninstalling the mixer, and a transport securing device that prevents the container from being undesirably opened during transport or storage.

The last-mentioned function is achieved in that a plunger rod, which is assigned to the plunger means, is accommodated in a displaceably guided manner in a retaining section, which faces away from the mixer, of the container in such a manner that the plunger rod does not notably project out of the retaining section of the container. In other words, the plunger rod ends essentially flush with the front side of the retaining section which faces away from the mixer. The feature of the plunger rod being provided flush with the front side of the retaining section, which faces away from the mixer, of the container is below understood to mean not only an exactly flush ending (i.e. an embodiment with the end of the plunger rod and the front side being in a common plane), but rather also that the plunger rod projects by a few millimeters, preferably not more than approximately 1 to approximately 2 mm, beyond the front side of the retaining section. In the case of this configuration, the container is also suitable for use with a discharge gun or a dispenser of the abovementioned type, for example with a 'Centrix®' gun. In contrast, it is unimportant for the function of the transport securing device whether the plunger rod is slightly set back with respect to the front side of the retaining section which faces away from the mixer. At most this limits the possibilities for completely emptying the container.

If the mixer is pre-installed on the container in accordance with the invention, the container can be taken directly into use without time-consuming installation steps. A pre-installed mixer is understood to be a mixer, in particular a static mixer, which is already provided, in the delivery state of the container, in a position on the container which is essentially also suitable for discharging the components. This does not exclude the possibility that, if appropriate, the mixer or a mixing tube and/or a discharge tube of the mixer must be turned and/or displaced slightly relative to the container in order to open the container prior to the first use of the container. However, it is preferred if the mixer is pre-installed on the container in such a manner that the mixer is already located in its end position which is suitable for discharging the components.

The use of the container is further simplified according to the invention in that the sealing means can be opened without uninstalling the mixer. The pre-installed mixer does not therefore have to be first removed from the container in order to open the sealing means. It is rather preferred if the sealing means is configured in such a manner that it allows an intuitive opening of the container. An intuitive opening of the container is to be understood as meaning a freeing (opening) of a flow connection between the chambers and the mixer, which takes place without separate opening steps, in particular by simply pushing the plunger rod or the plunger means forward. According to a particularly preferred embodiment of the invention, the sealing means is configured in such a manner that it frees (opens) the flow connection between the chambers and the mixer automatically, that is, without additional actuation by the user, when the plunger means is actuated, in particular as a function of the internal pressure in the chambers. This includes for example a defined bursting of the sealing means, an elastically flexible sealing means which frees the flow connection, and/or the displacement of a sealing means, the mixer or a discharge tube of the mixer.

Particularly good sealing of the container with at the same time simple opening can be achieved by at least one of the chambers having a discharge opening, which is assigned a sealing plunger as a sealing means, which can be moved from a position which seals the discharge opening to a position which opens the discharge opening by the pressure of the components to be discharged.

This can take place in particular in that at least one of the chambers has a preferably channel-like discharge opening, which has a first region with a reduced cross-sectional area and a further section with a widened cross-sectional area, to which is assigned a sealing plunger for sealing and freeing the discharge opening, which plunger can be displaced from the first region into the second region, as a sealing means with a contour which is at least in sections congruent with the first region, so that the sealing plunger, in a position displaced from the first region into the second region, frees (opens) a flow connection between the chambers and the mixer. In other words, the sealing plunger closes in a sealing manner the first region of the discharge opening while the container is being transported and stored. Before or during the first use, the sealing plunger is then displaced from the first region into the second region so that the components can flow through and/or around the sealing plunger into the mixer. The basic functioning of the opening of a container is described in DE 102 54 409 A1.

A reduction in the cross-sectional area in the first region of the discharge opening can for example be made by radially inwardly projecting projections being provided in the discharge opening. Alternatively or in addition to this, a central peg or web, which defines a for example annular space, can also be provided in the discharge opening. The sealing plunger is then correspondingly provided with lateral recesses and/or a central opening.

As an alternative to this, it is also possible for the sealing means and the mixer to be configured in such a manner that the sealing means frees (opens) a flow connection between the chambers and the mixer automatically when there is a rotational and/or displacement movement of the mixer relative to the chambers. This can take place for example by one or a plurality of discharge openings of the chambers not being aligned flush with corresponding inlet openings of the mixer when the mixer is in its pre-installed state.

It is preferred if the mixer is fixed releasably to the container and/or to at least one discharge opening of the chambers. The container can however also have a mixer for single use, which is fixed non-releasably or even integrally to the container and/or to a discharge opening of the chambers. The mixer can in this case be a preferably static or dynamic mixer or an applicator, in which the components are mixed with each other before being discharged.

A retaining section is provided on the side of the container which faces away from the mixer, in which retaining section a plunger rod is guided in a displaceable manner. This retaining section has a first region with a smaller outer diameter and an adjacent second region with a larger outer diameter which faces away from the mixer. In this case the first region can be longer in the axial direction of the container than the second region, which can be configured for example in an approximately flange-like manner. This second region with an enlarged outer diameter supports the function of the transport securing device of the container according to the invention, in that an inadvertent opening of the container is prevented in the event that the latter is subjected to a jolt in the direction in which the plunger rod is pushed forwards during transporting or storage. By providing the plunger rod flush with the front side of the second region of the retaining section the plunger rod can no longer accidentally be pushed into the container, which could lead to an opening of the container.

A particularly expedient arrangement of the chambers in the container is the coaxial provision of the chambers, so that one chamber surrounds the other chamber. The chambers can however also be arranged behind each other and/or next to each other.

Independently of the features mentioned beforehand, an essential aspect of the present invention lies in the fact that the plunger means of the container has a transfer tappet which has a plunger rod which is guided in the retaining section of the container and actuation sections for discharging the components from the chambers connected thereto. The actuation sections can in each case interact with a plunger which can be displaced in the chambers. In accordance with a particularly preferred embodiment of the invention, the transfer tappet is configured such that each chamber of the container is assigned a separate actuation section which projects from the plunger rod in the direction of the mixer. The handling of the container according to the invention is thereby further simplified, as two or more actuation sections can be pushed forward simultaneously by means of the advance of the one plunger rod of the transfer tappet, so that all chambers can be emptied at the same time. This also simplifies the use of the container according to the invention in a discharge device, for example a discharge gun, with only one displaceable tappet. In a development of this inventive idea, the plunger rod and the actuation sections of the transfer tappet can be formed integrally with one another.

Alternatively or in addition to the above-mentioned features, the container according to the invention can have an opaque housing in which the chambers for accommodating the components are provided. The container is in this case also suitable in particular for stable storage of light-sensitive components. In order to make it possible to check the filling level of the components, a window is preferably provided in the housing in this case, which window is arranged and configured in such a manner that a marking element assigned to the plunger means is visible through the window. The position of the marking element which is visible through the window indicates the filling level of the components in the container, with the storage stability of the components not being adversely affected by the window if its dimensions are selected to be such that it is situated exclusively on the side of the housing which faces away from the mixer and is separated from the chambers by the discharge plunger. A scale and/or grid can additionally be assigned to the window and/or the marking element in order for example to facilitate dosing.

The window can be configured as a separate, transparent or translucent element which is inserted in a slot or similar opening in the container. Alternatively to this, it is also possible to use a film as a window, which is fixed, for example adhesively bonded, over a slot or similar opening in the container. Such a film can be printed with a scale or the like and can bear additional information such as the name and use-by date of the product. In other words, a label film is also used as a window.

As a further alternative to a window in the container, the lid and/or the retaining section of the container can be configured to be at least partially transparent or translucent and thus as a window. If the transfer tappet, which can be moved in the retaining section, is provided with a for example coloured marking, the filling level of the container can be checked without a for example slot-like window being provided in the housing of the container.

According to a preferred embodiment of the invention, the mixer is a static mixer with a mixing element for moving around (deflecting) the components to be mixed and with a (discharge) tube which surrounds the mixing element. In this case, spring arms are provided preferably integrally with the housing of the container, which project in the axial direction towards the mixer and have radially inwardly projecting ribs, for example catch hooks or projections, with which the tube can be locked in place on the housing. In this way the mixer or the (discharge) tube can be pre-installed particularly simply on the housing of the container so that the mixer does not have to first be attached to the container with additional effort before the container is first used.

The mixing element can basically be configured as a mixer helix or as a for example rectangular labyrinth element, with it being possible for the (discharge) tube to then be configured correspondingly with an angled cross section. In this case the mixing element can be connected integrally or in another suitable manner to the housing of the container or assigned to the (discharge) tube. To this end, the mixing element can also be connected to the (discharge) tube, for example by means of securing in place, in order to be able to install or uninstall the mixer as a unit. Examples for the configuration of a mixing element are described in U.S. Pat. No. 4,538,920, EP 1 550 512, WO 2004/052519, EP 1 426 099, WO 2006/039827, EP 1 029 588, EP 0 749 776, EP 1 588 757 and EP 0 815 929.

The container can be opened particularly simply in that the mixer has a mixing element for moving the components to be mixed around and a tube which can be displaced in the axial direction relative to the mixing element, to which tube a sealing means is assigned for sealing the chambers. This sealing means can for example be formed by stopper-like sealing plungers, which are inserted into discharge openings or channels of the chambers when the container is sealed. To open the chambers, these sealing plungers can be pulled out by a relative movement of the tube to the mixing element out of the discharge openings or channels, so that a flow connection between the chambers and the mixer is freed. To this end, the sealing plungers can be configured integrally with the (discharge) tube or be fixed to it. In other words, according to the invention only a relative movement needs to take place between the tube and the housing or the mixing element in order to open the container, with for example the tube being pulled forward from the housing and the mixing element in the discharge direction or being pushed forward by the pressure of the components. In this case, the engagement of a sealing plunger or peg with a sealing collar or the like of the tube can be disengaged by the relative movement, or the sealing plunger or peg remains stationary while the sealing collar or the like of the tube is moved away. The channel freed by this does not have to run in the axial direction, but rather can also run laterally, that is, in the radial direction, for example.

In particular in the case of containers which are intended for multiple use with a replaceable mixer or similar applicator, it is preferred if the mixer can only be placed onto the container in one single alignment so that a defined assignment of outlet channels or the like in the container and corresponding inlet channels or the like in the mixer takes place. This can preferably take place by means of coding and/or alignment means which, for example, can be configured as suggested in EP 0 598 965, EP 0 723 807 or EP 0 730 913, that is to say, the coding takes place by means of projections and recesses that match one another on the mixer and the container. Alternatively or in addition to this, a defined alignment of mixer and container with one another can also be achieved, in that the contour of the outlet connecting piece and/or of outlet channels of the container and a corresponding opposite contour or inlet channels of the mixer only permit installation of the mixer in a single alignment relative to the container.

The invention further relates to a combination of a container of the above-described type and a discharge device for it. In this case the discharge device has a receptacle at least for the retaining section of the container and a tappet which can be displaced relative to the container, the outer diameter of which tappet is less than or equal to that of the plunger rod of the container. The displaceable tappet can thus penetrate the retaining section and thereby push the plunger rod of the transfer tappet forward. The discharge device can in this case be configured as a manually and/or power-operated discharge gun or for example as a syringe. The discharge device is preferably suitable for multiple use, whereas the container can be a single-use container or likewise a refillable container.

The invention is explained in more detail hereinafter on the basis of exemplary embodiments and with reference to the drawings. All described and/or pictorially represented features form the subject of the invention per se or in any desired combination, independently of their summarization in the claims or back references thereof. In the figures:

FIG. 1 schematically shows a container according to the invention in accordance with a first embodiment in a perspective view, FIG. 2 schematically shows the container according to FIG. 1 in an exploded view, FIG. 3 schematically shows a sectional view of the container according to FIG. 1, FIG. 4 schematically shows a further sectional view of the container according to FIG. 1 without a mixer, FIG. 5 schematically shows a further sectional view of the container according to FIG. 1 without a mixer in the closed state, FIG. 6 schematically shows a further sectional view of the container according to FIG. 1 without a mixer in the opened state, FIG. 7 schematically shows a container according to the invention in accordance with a second embodiment in an exploded view, FIG. 8 schematically shows a sectional view of the container according to FIG. 7, FIG. 9 schematically shows a further sectional view of the container according to FIG. 7 without a mixer, FIG. 10 schematically shows a container according to the invention in accordance with a third embodiment in an exploded view, FIG. 11 schematically shows a sectional view of the container according to FIG. 10, FIG. 12 schematically shows a sectional view of the container according to FIG. 10 without a mixer, FIG. 13 schematically shows a container according to the invention in accordance with a fourth embodiment in a perspective view, FIG. 14 schematically shows the container according to FIG. 13 in an exploded view, FIG. 15 schematically shows a sectional view of the container according to FIG. 13, FIG. 16 schematically shows a container according to the invention in accordance with a fifth embodiment in an exploded view, FIG. 17 schematically shows a sectional view of the container according to FIG. 16, FIG. 18 schematically shows a container according to the invention in accordance with a sixth embodiment in an exploded view, FIG. 19 schematically shows a sectional view of the closed container according to FIG. 18, FIG. 20 schematically shows a sectional view of the opened container according to FIG. 18, FIG. 21 schematically shows a container according to the invention in accordance with a seventh embodiment in an exploded view, FIG. 22 schematically shows a sectional view of the closed container according to FIG. 21, FIG. 23 schematically shows a sectional view of the opened container according to FIG. 21 and FIG. 24 schematically shows a container according to the invention in accordance with an eighth embodiment in a sectional view.

FIGS. 1 to 6 show a container 1 configured as a mini-cartridge. The mini-cartridge is in turn configured with a housing 2, which is essentially cylindrical on the inside and the outside, and a lid 3, which closes the housing at the back and can be secured in place on the housing. Two chambers 4a and 4b, which each have an approximately semi-circular cross section, are formed within the housing. The volume of the chambers can be reduced in a defined manner by means of a plunger rod arrangement 15, which extends partially through the lid 3, which is secured in place on the housing 2, and partially projects into the two chambers 4a, 4b.

A coupling means 6 with a locking ring 7 for releasable fixing of a mixer 8 is provided on the front side of the chambers 4a, 4b, which faces away from the lid 3. The locking ring 7 is secured firmly in place on the container 1 and can be rotated relative to the container 1 between a position which frees the coupling means 6 for installing or uninstalling the mixer 8 and a position which blocks the coupling means 6, in which the mixer 8 is locked firmly in place on the container 1, as is described in more detail in DE 10 2007 044 983.

The mixer 8 is configured in the embodiment shown as a discharge tube 8a with a mixer helix 8b, that is as a static mixer. In the delivery state of the container 1 shown in FIG. 1, the mixer 8 is already pre-installed on the container 1 in such a manner that the container can be put into use without further installation steps.

The two adjacently arranged chambers 4a, 4b each have a discharge opening 9a, 9b, which open into a common discharge connecting piece 10, which is configured to have an approximately oval cross section in the embodiment shown. The mixer 8 is correspondingly provided with an inlet opening, which is likewise essentially oval-shaped to be able to be inserted into the discharge connecting piece 10. The inlet opening is subdivided into two sections by a separating element so that the components which are discharged from the chambers 4a, 4b can be guided separately from each other as far as the mixer helix 8b of the mixer, as described in more detail below.

Figures 1, 3:
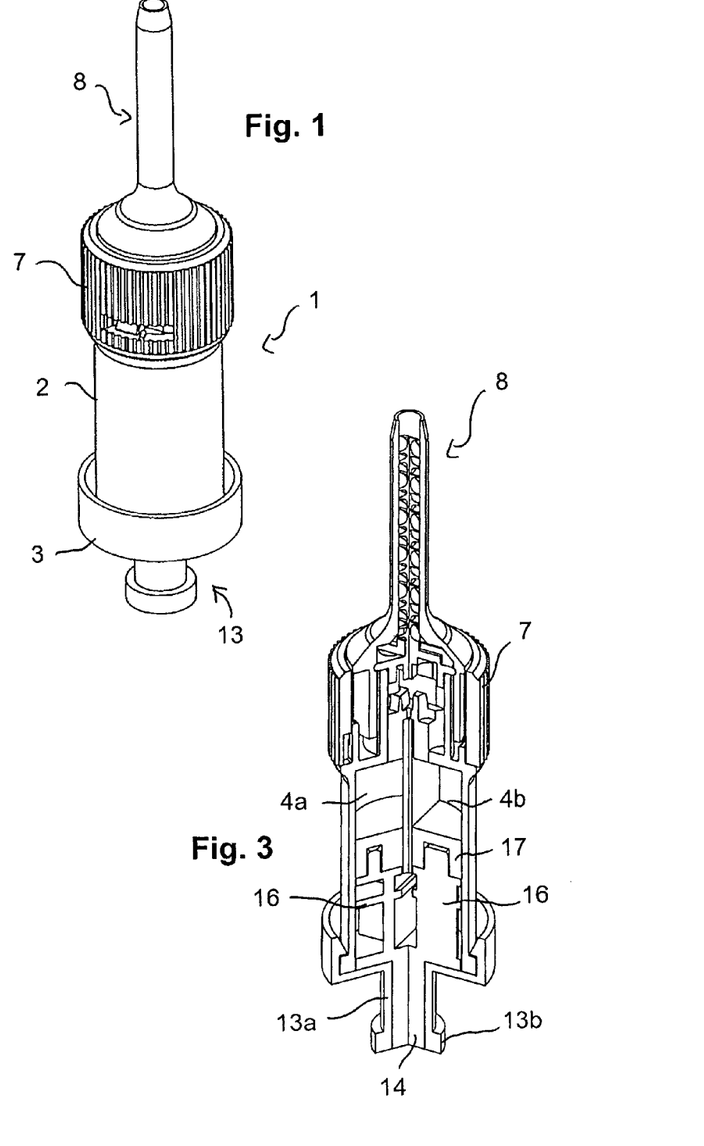
Figure 2:
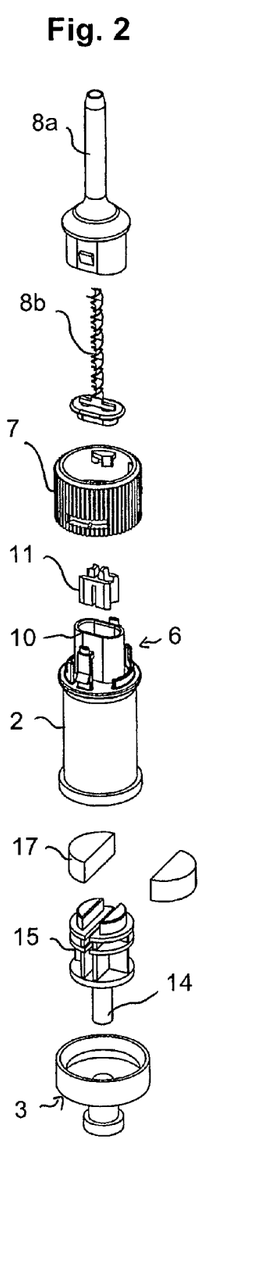

In the delivery state which is also shown in FIG. 3, the two chambers 4a, 4b are sealed by a sealing plunger 11, which has two sealing blocks which project backwards from a transverse wall, that is away from the mixer 8, the outer contour of which sealing blocks is matched to the inner contour of the discharge openings 9a, 9b. In the illustration according to FIGS. 4 and 5, the sealing blocks project into the discharge openings 9a, 9b and seal them. A gap-like space is formed between the two sealing blocks, which space is matched to the rectangular contour of a separating wall 12 which is provided between the two discharge openings 9a, 9b within the discharge connecting piece 10. The sealing plunger 11 can thus be displaced in a guided manner on the separating wall 12 from the closed position shown in FIG. 5 and axially forwards into the discharge connecting piece 10, into the opened position shown in FIG. 6, by means of which the two discharge openings 9a, 9b are freed (opened). The components can thus flow from the chambers 4a, 4b through the discharge openings 9a, 9b and past the sealing plunger 11 into the discharge connecting piece 10 and into the mixer 8. The discharge openings 9a, 9b thus form a region with a reduced cross-sectional area, which region can be sealed by the sealing plunger 11, while the adjoining discharge connecting piece 10 forms a region with an enlarged cross-sectional area for accommodating the sealing plunger in the opened position of the sealing means.

Figures 5, 6:
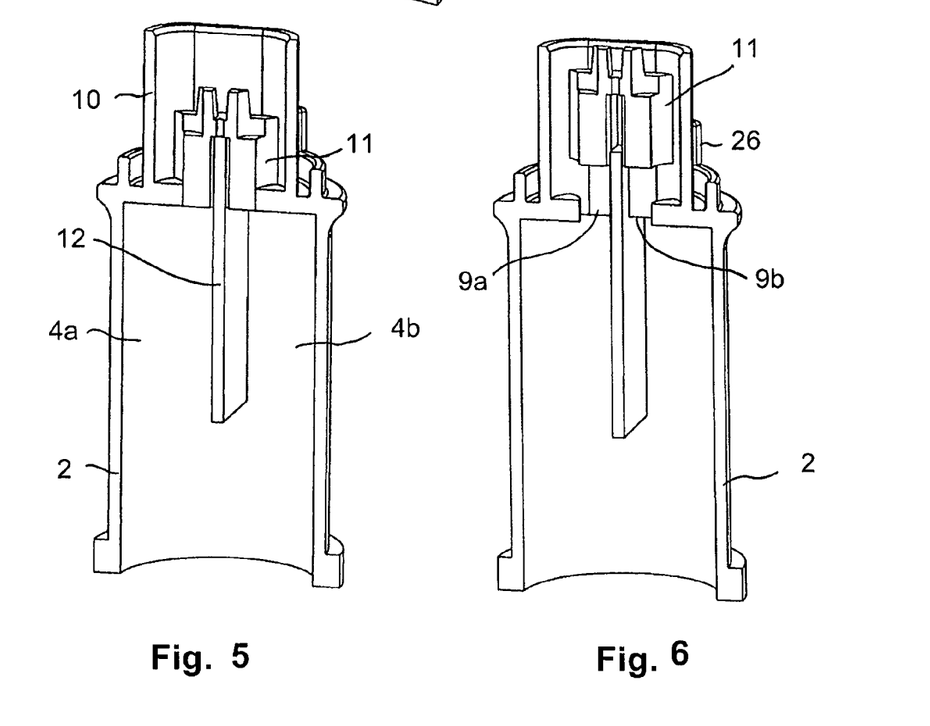

In order to allow the sealing plunger 11 to be displaced on the separating wall 12, a ventilation opening is provided in the transverse wall of the sealing plunger 11, and semi-circular ventilation channels are likewise formed in the sealing blocks adjacent to the space which accommodates the separating wall 12 in the closed state. This means that the sealing plunger 11 can be set and pushed on the separating wall 12. Projections are formed on the sealing plunger 11 on the side opposite the two sealing blocks, which projections interact with the inlet opening of the mixer 8 in such a manner that the components discharged from the chambers 4a, 4b are directed separately from each other to the mixer helix 8b of the mixer 8.

The lid 3 of the container 1 is provided with a retaining section 13 which is central in the embodiment shown and projects away from the container on the side facing away from the mixer 8. The retaining section has a first, approximately cylindrical region 13a and a second region 13b, which faces away from the mixer 8 and has an outer diameter which is enlarged in a flange-like manner with respect to the first region 13a. The retaining section 13 is thus suitable for fixing the container in a discharge gun according to EP 1 256 389 A2.

Figure 4:
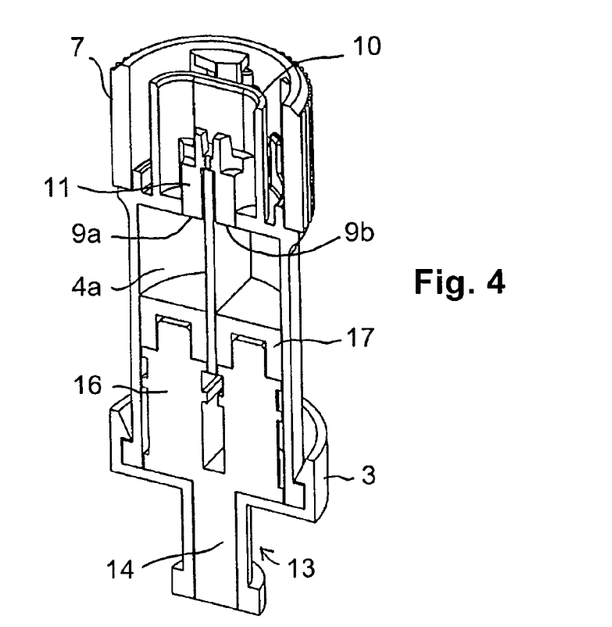

The retaining section 13 is provided with a through-opening, in which a plunger rod 14 of a transfer tappet 15 is displaceably guided in such a manner that the end of the plunger rod 14 is flush with the front side of the second region 13b in the delivery state shown in FIGS. 1, 3 and 4. In other words, in the delivery state the end of the plunger rod 14 and the front side of the second region 13b are located in a common plane. The transfer tappet 15 has two actuation sections 16, which are each assigned to a chamber 4a, 4b. The two actuation sections 16, which are at a distance from each other, project in the direction of the mixer 8 away from the plunger rod 14 into the chambers, in which discharge plungers 17 are accommodated in a displaceable manner. The transfer tappet 15 therefore has the effect of pushing the discharge plungers 17 of both chambers 4a, 4b forward at the same time when the plunger rod 14 is pushed into the through-opening of the retaining section 13.

Figures 7, 8, 9:
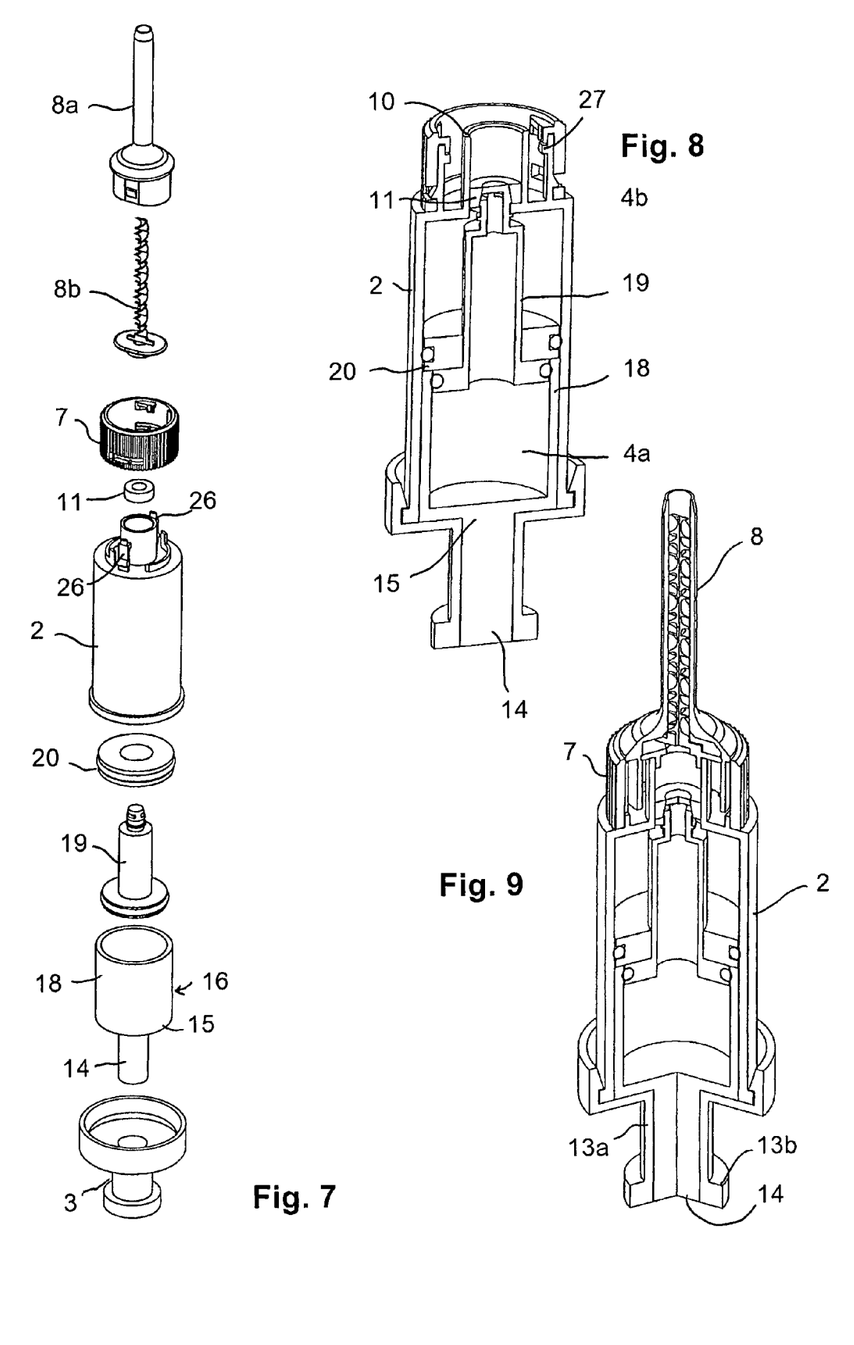

FIGS. 7 to 9 show a further embodiment of a container according to the invention, which has two chambers 4a, 4b, which are arranged one behind the other when viewed in an essentially axial direction. The first chamber 4a is formed by a plunger 18, which is cylindrical in sections, and a discharge insert 19. The second chamber 4b is essentially delimited by the housing 2 of the container itself, in which the cylindrical plunger 18 is also guided in a displaceable manner, and a plunger 20, which surrounds the discharge insert 19 in an annular manner.

The discharge openings of the two chambers 4a, 4b open into a common discharge connecting piece 10, which forms a common discharge opening for both components. A sleeve-like point of the discharge insert 19 projects into the region of the discharge connecting piece 10 which is at the bottom in FIGS. 8 and 9, and thus reduces the cross-sectional area of the discharge connecting piece 10. An annular sealing plunger 11 is provided in this region, which plunger sits on the point of the discharge insert 19 in the position according to FIG. 8 in such a manner that it seals the discharge opening of the chamber 4b.

In order to open the container 1, the sealing plunger 11 can be pushed forwards in the axial direction, that is to say, towards the mixer 8, within the discharge connecting piece 10 by the pressure of the component contained in the chamber 4b, in order thereby to open both discharge openings of the chambers 4a and 4b. The components can thereby flow together through the central opening in the annular sealing plunger to the mixer 8. The mixer 8 is fixed by means of a coupling means 6 and a locking ring 7 to the container 1 in this embodiment, as described above.

In order to dispense the components contained in the chambers, the cylindrical plunger 18 is pushed forward in the direction of the mixer 8. The volume in the chamber 4a is, on the one hand, thereby reduced so that the component accommodated therein is delivered through the discharge insert 19 to the discharge connecting piece 10, while at the same time an axially forward front side of the cylindrical plunger 18 pushes the plunger 20 forward so that the volume of the chamber 4b is also reduced and the component accommodated therein is likewise delivered to the discharge connecting piece 10 and the mixer.

As can be seen in FIGS. 8 and 9, the plunger 20 is sealed with respect to the outer cylindrical housing wall 2 of the two chambers by means of a sealing ring. In the same manner, the discharge insert 19 is sealed with respect to the cylindrical plunger 18 by means of a sealing ring.

Figures 10, 11, 12:
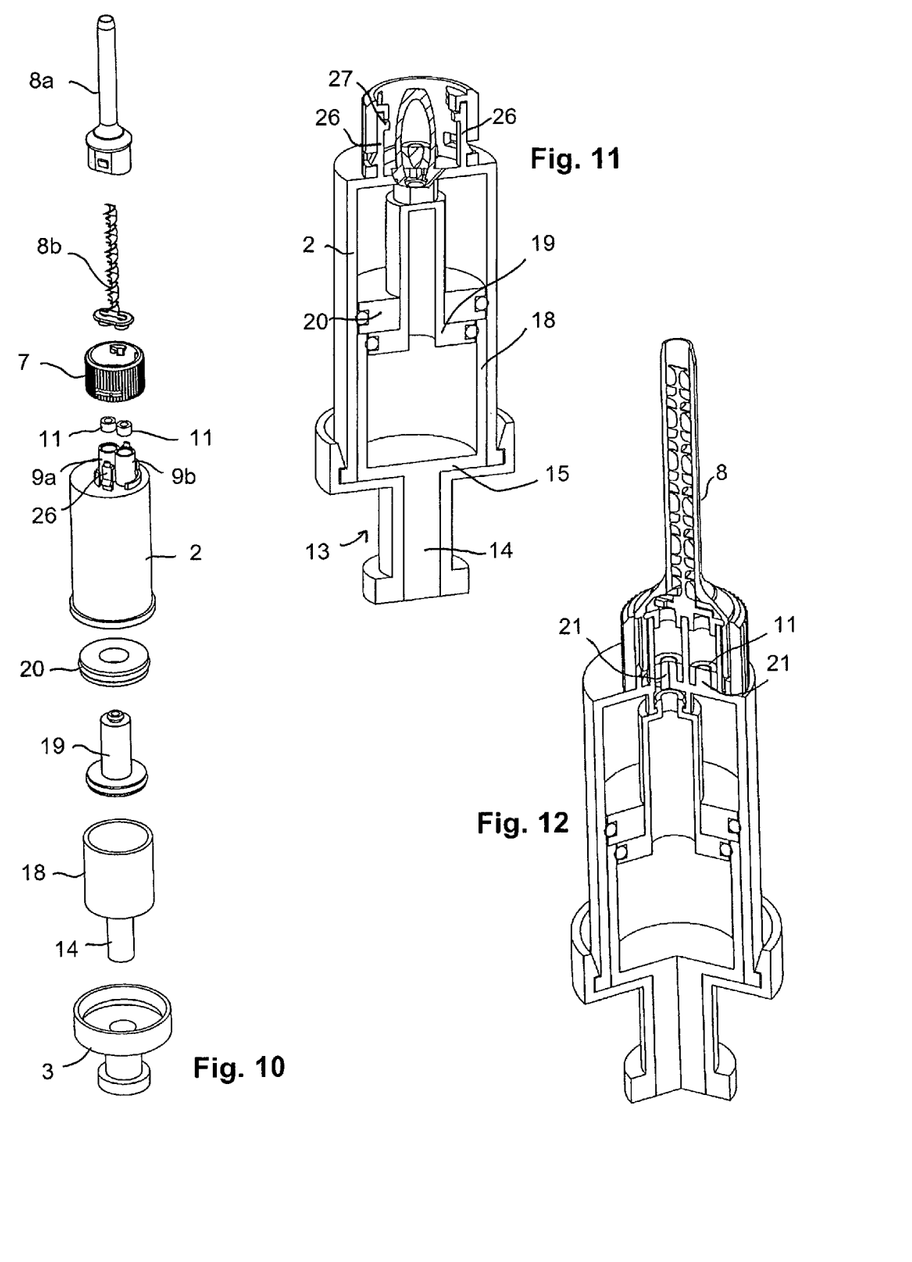

An embodiment which is similar to the above-described embodiment in terms of the construction of the container is shown in FIGS. 10 to 12. The discharge openings of the two chambers 4a, 4b, which are again arranged one behind the other, do not however open into a common discharge connecting piece 10 here, but rather two separate channel-like discharge openings 9a, 9b are provided, which are respectively sealed by separate annular sealing plungers 11. These sealing plungers sit in the closed state shown in FIGS. 11 and 12 on peg-shaped projections 21 in the discharge openings 9a, 9b and can be pushed away from the projections 21 by the pressure of the components during discharge in the direction of the mixer 8, so that the components can flow through the central openings of the respective sealing plunger 11.

Owing to the central arrangement of the discharge insert 19, an eccentric arrangement of the discharge opening 9b for the component accommodated in the chamber 4b is produced. The mixer 8 is also correspondingly placed eccentrically on the two chambers. The coupling means 6 for releasable connection of the mixer 8 is also eccentrically arranged in the same manner.

Figures 13, 14, 15:
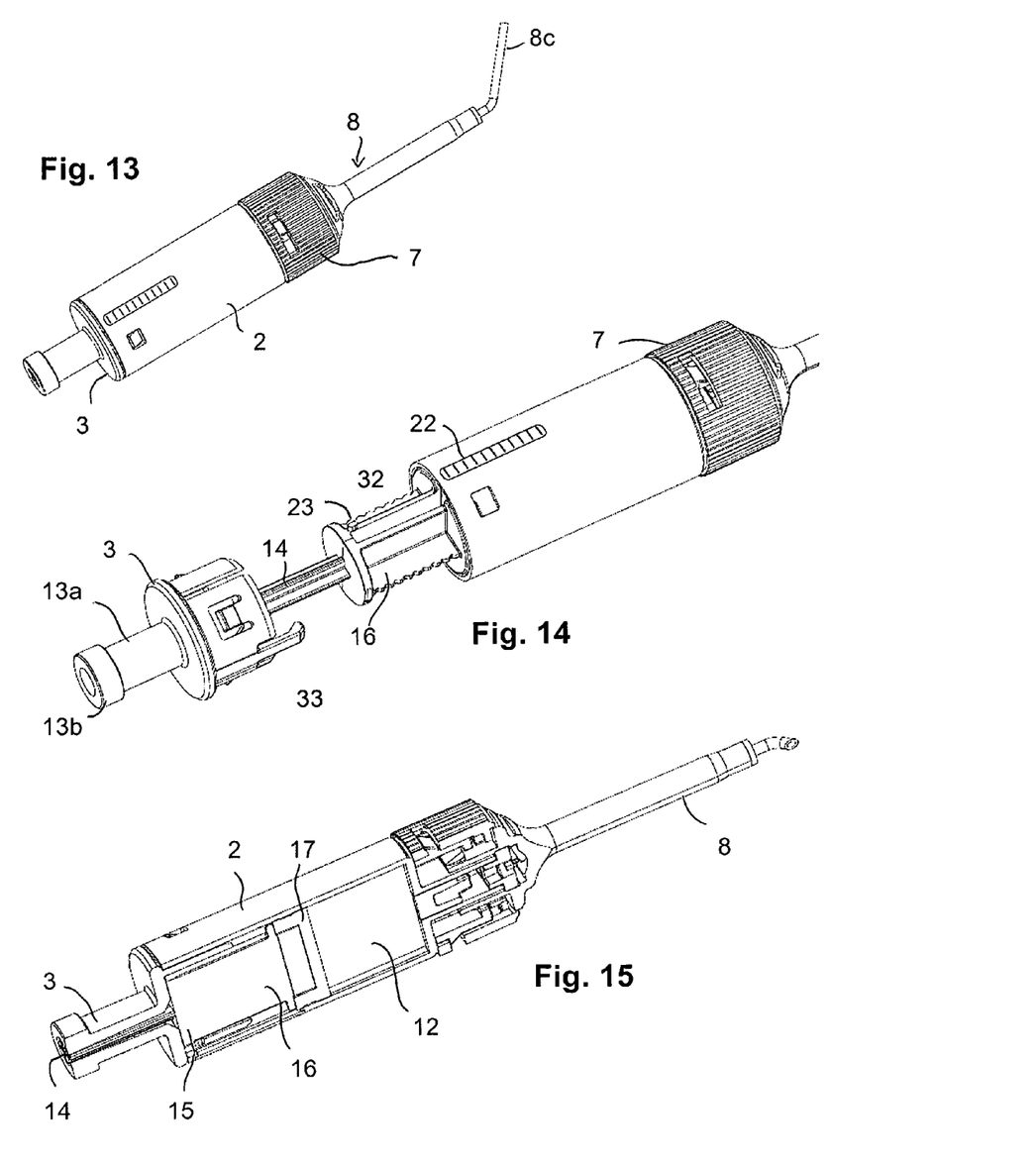

A further embodiment of the invention is shown in FIGS. 13 to 15, wherein the basic structure of the container corresponds to that according to FIGS. 1 to 6. A translucent or transparent window 22 is provided in the housing 2, which in this embodiment consists of an opaque material, in the rear region which faces away from the mixer 8, which window extends in the axial direction of the container. A marking element 23, for example a coloured dot or projection, is assigned to the window 22 on the transfer tappet 15 in such a manner that the marking element 23 is visible through the window 22 from the outside. If the transfer tappet 15 is now pushed in order to discharge the components in the container 1, then the position of the marking element 23 in the window 22 changes and therefore allows the filling level of the container to be monitored. To this end, the window 22 is provided with a scale.

Since the chambers in which the for example light-sensitive components are accommodated are sealed by the discharge plunger 17 in the direction of the window 22, the storage stability of the components is not adversely affected by the window 22.

In order to allow the marking element 23 to be inspected in the window 22 over the entire displacement path of the transfer tappet 15, the fixing of the lid 3 to the housing 2 is changed in such a manner compared to the embodiments according to FIGS. 1 to 12 that the lid 3 does not grasp the housing but can be pushed into it and secured in place there.

The mixer 8 is provided with an additional discharge tube 8c, which facilitates application of the mixture emerging from the mixer 8, for example for dental uses.

Figure 16:
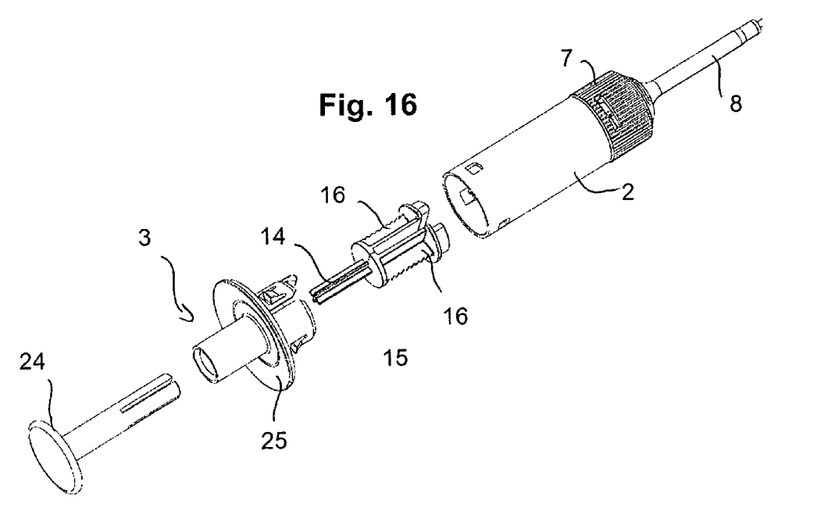
Figure 17:
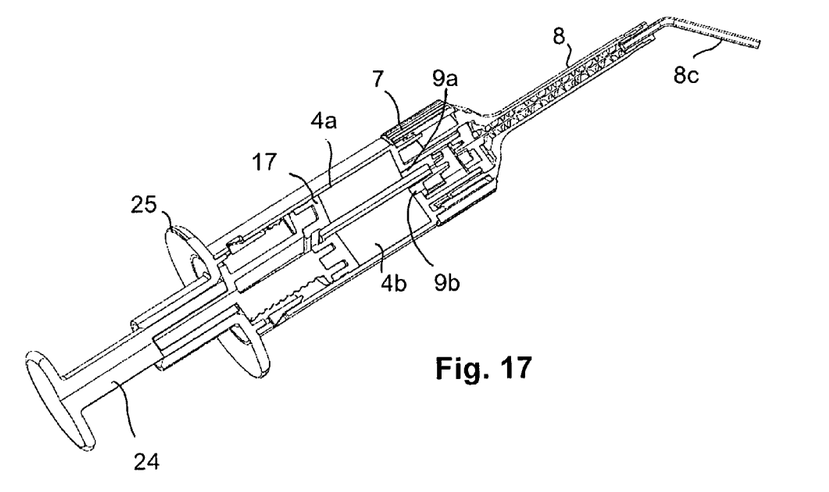

The syringe-like discharge of the components from the container 1 by means of a tappet 24 is possible in a particularly simple manner if the lid 3 has a flange-like edge 25, as shown in the embodiment according to FIGS. 16 and 17. The tappet 24 and the plunger rod 14 have contours which are matched to each other, so that the plunger rod 14 and the tappet 24 can be guided together in the sleeve-like guide section of the lid 3. In order to discharge the components, the tappet 24 is supported in such a manner that it grasps the plunger rod 14 on a wall of the transfer tappet 15, which wall connects the actuation sections 16.

The mixer 8 is fixed to the housing 2 in the embodiments shown by means of a coupling means 6, which has two spring arms 26, which are configured to be integral with the housing 2 and project away from a front side of the housing 2 in the discharge direction adjacent to the discharge connecting piece 10 or adjacent to the discharge openings 9a, 9b. Radially inwardly projecting ribs 27 are provided as catch projections on the spring arms 26, which ribs can grip behind the corresponding gripping faces of the discharge tube 8a in order to fix it to the housing 2. The spring arms 26 can bear against the discharge tube 8a in a defined manner or be spread in order to lock or free the discharge tube 8a of the mixer 8 by means of the locking ring 7.

Alternatively to the embodiment shown in FIGS. 1 to 17, the spring arms 26 can also be configured and arranged in such a manner that the discharge tube 8a can also be fixed to the container 2 without the locking ring 7, by the spring arms 26 being spread apart when the discharge tube 8a is placed on and the ribs 27 snapping behind the gripping faces of the discharge tube 8a.

The above-described embodiments show in each case containers with two chambers 4a, 4b, so that these containers 1 are suitable for storing and at the same time discharging two components (two-component systems), for example a base mass and a catalyst of a hardenable dental mass. In principle, more than two chambers can also be provided in order to discharge a greater number of different components. Furthermore, the various arrangements of the chambers can be combined with each other and different volume ratios of the individual chambers can be selected.

Embodiments are shown in FIGS. 18 to 23, in which the chambers 4a, 4b are arranged coaxially in such a manner that one chamber 4a surrounds the other chamber 4b (tube-in-tube system). The transfer tappet 15 is configured with a central first actuation section 16a, which projects away from the plunger rod 14 and a sleeve-like second actuation section 16b, which surrounds the first section. The spring arms 26 are configured in such a manner in this embodiment that the discharge tube 8a can be fixed by snapping on.

Figures 18, 19:
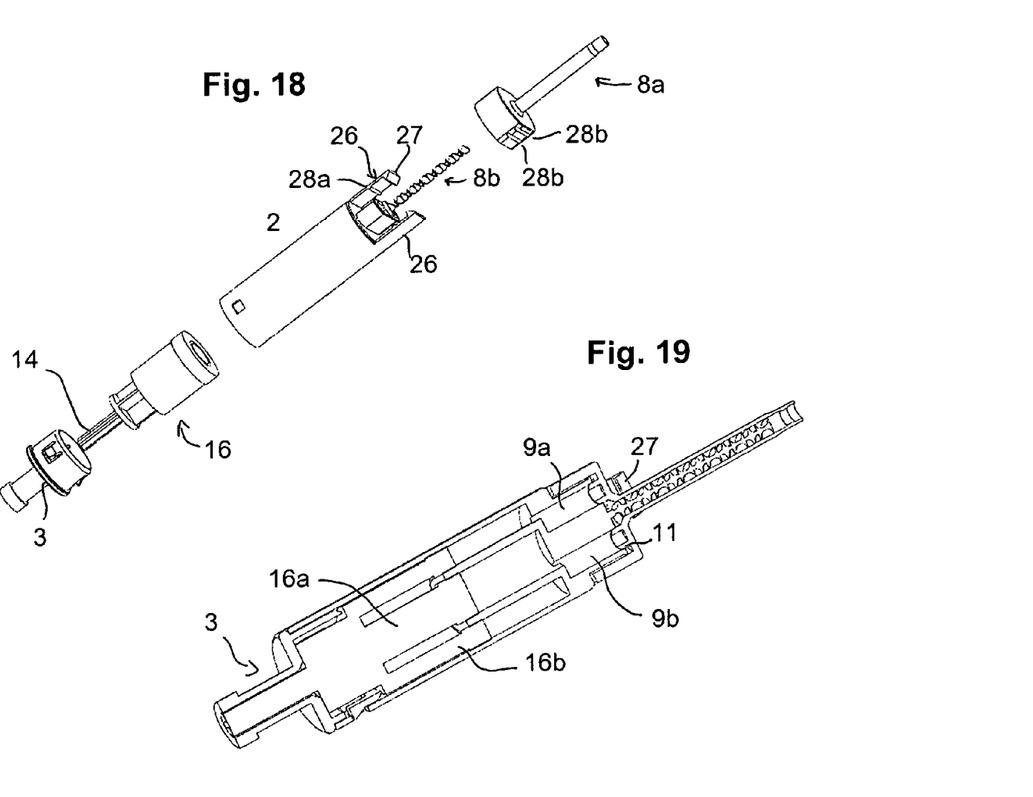
Figure 20:
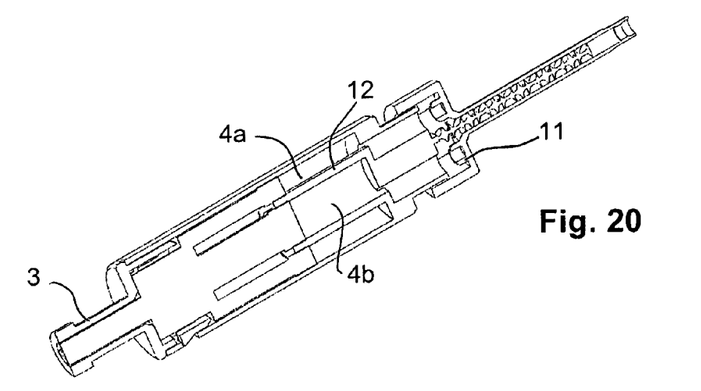

The discharge tube 8a in the embodiment of FIGS. 18 to 20 can be displaced relatively to the mixer helix 8b, which is fixed permanently to the housing 2, in order to open or seal the container. This takes place by means of a sealing plunger 11, which is fixed to the discharge tube 8a and is configured as a sealing collar, which projects into the discharge openings or the discharge connecting piece 10 in the sealed position of the container. To open the container, the discharge tube 8a is pushed or pulled forward together with the sealing plunger 11 in the discharge direction, so that the sealing plunger frees the discharge openings or the discharge connecting piece 10. The spring arms 26 have catch hooks 27 on their side facing away from the lid 3, which catch hooks grip behind the discharge tube 8a of the mixer. Furthermore, a catch projection 28a is provided on each of the spring arms 26, which can come into contact with two catch recesses 28b on the discharge tube 8a, which are spaced apart from each other axially. The container is closed when the catch projections 28a engage in the front catch recesses 28b in the discharge direction (FIG. 19), that is, the discharge tube 8a is drawn back in the direction of the lid 3, and the container is open, when the catch projections 28a engage in the rear catch recesses 28b in the discharge direction (FIG. 20), that is, the discharge tube 8a is pushed or pulled forward in the discharge direction.

Figures 21, 22:
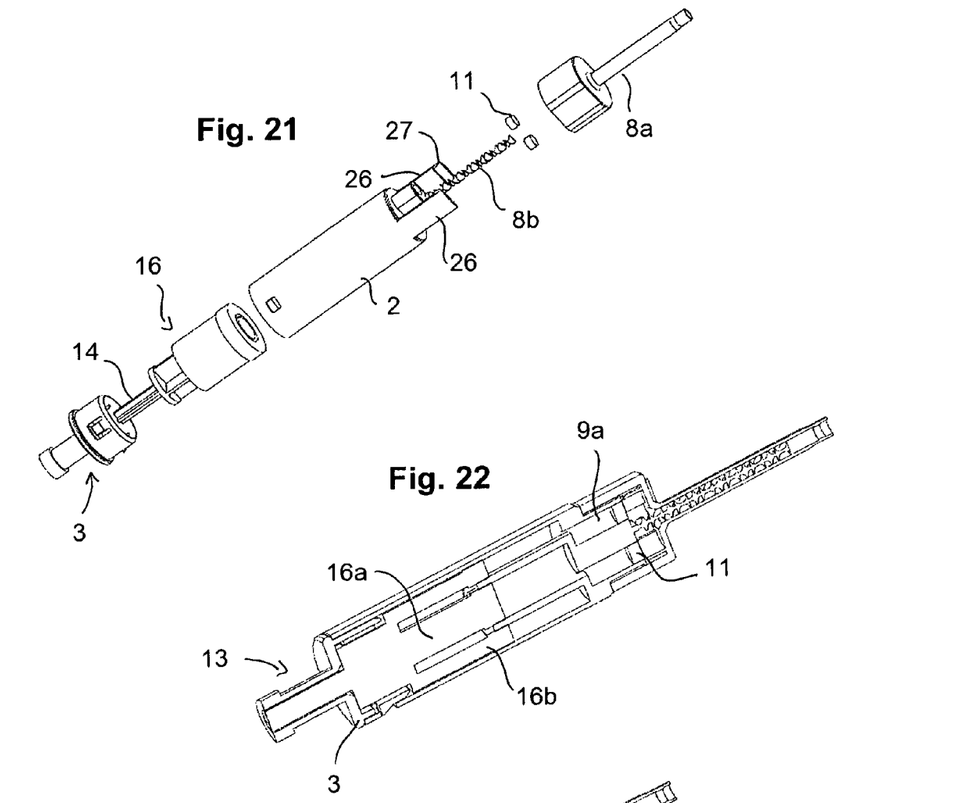
Figure 23:
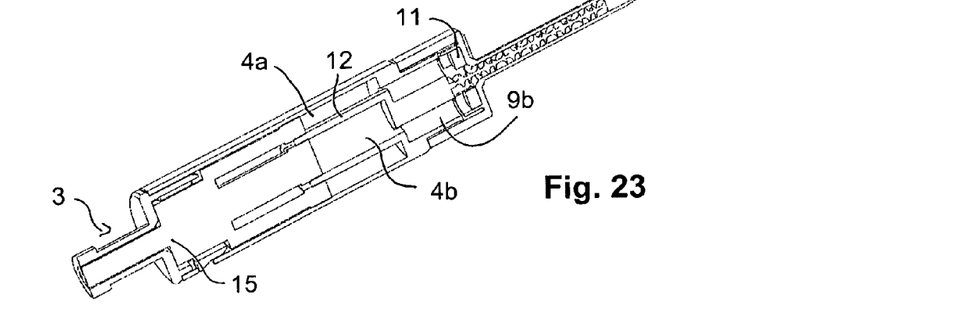

In contrast, the discharge tube 8a in the embodiment of FIGS. 21 to 23 is fixed firmly, that is, non-displaceably, to the container by means of the catch hooks 27 of the spring arms 26. The container is sealed or opened by means of sealing plungers 11, which are placed in the discharge openings 9a, 9b in the closed state of the container (FIG. 22). The sealing plungers 11 can be pushed forward into a space in the discharge tube 8a by the pressure of the components in the chambers (FIG. 23), so that the components can flow past the sealing plungers 11 into the discharge tube 8a.

The details of the above-described embodiments can be combined and/or exchanged with each other in accordance with the requirements of the container. A retaining section 13, a window 22 and/or a flange-like edge 25 can thus be provided on each container. Furthermore, each container can be assigned a tappet 24 for discharging the components or a suitable gun, or the mixer and its fixing can be configured as in FIG. 18. In addition, the discharge tube 8a can be fixed by means of spring arms 26 which are provided on it and grip a corresponding structure on the housing 2 of the container.

Figure 24:
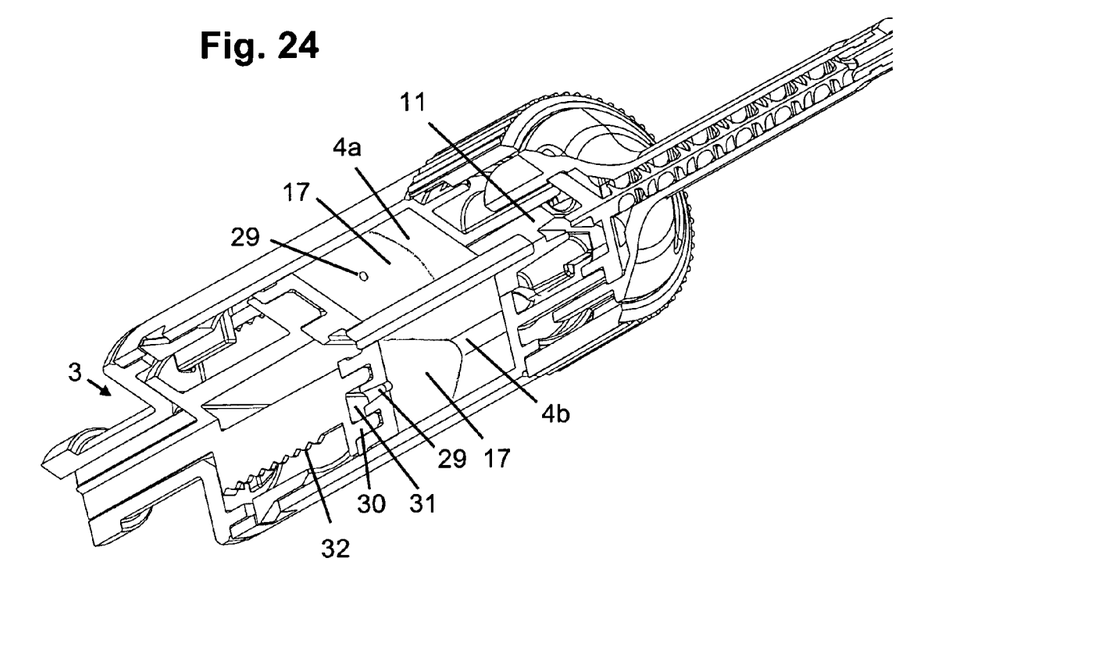

In contrast to the embodiments of FIGS. 1 to 6, the mixer-side sealing plunger 11 is configured without a ventilation opening in FIG. 24. In this case the two chambers 4a, 4b are sealed by the sealing plunger 11 before filling and then filled from the side facing away from the mixer. The discharge plungers 17 are each configured with a ventilation opening 29 so that residual air can escape through the discharge plungers 17 when they are inserted into the chambers 4a and 4b. To seal the ventilation openings 29 of the discharge plungers 17, annular projections 30 can be formed on the front-side of the actuation sections 16 of the transfer tappet 15, which sections are connected to the discharge plungers.

The projections 30 consist essentially of a closed, circumferential wall, which encloses a hollow 31 which is open in the direction of the discharge plungers 17. The wall of each projection 30 interacts in a sealing manner with a corresponding rear wall on the discharge plungers 17, in order to seal the ventilation openings 29 in this manner. Excessive material, which may be present and have emerged from the ventilation openings 29, can be accommodated in the hollows 31.

In FIG. 14, a tooth-like profile 32 is provided on actuation sections 16 of the transfer tappet 15, which profile interacts with a catch hook 33 formed on the lid 3, in order to give the user tactile feedback during the process of dispensing the material from the chambers 4a, 4b. This also facilitates the dosing of the material during dispensing. In the embodiment according to FIG. 14, the notches on the actuation section 16 and the raised parts between them are configured uniformly, that is to say, have the same depth and height respectively.

In contrast to this, in FIG. 24 the first raised part on the actuation section 16, which part the point of the catch hook 33 (FIG. 14) must pass on first use of the container, is configured to be shallower or is omitted completely in order to obtain a greater installation tolerance and to reduce the initial resistance when discharging the components from the container. In addition, the second raised part on the actuation section 16, which part the point of the catch hook 33 must pass on first use of the container, can be configured to be steeper or larger in order to present a resistance to an initially great force for discharging the components from the containers. In this manner, an excessively large amount of the components is prevented from being inadvertently discharged in the event of a sudden release of the discharge plunger 17 on first use of the container.

The invention claimed is:

1. Container for storing and discharging at least two components, in particular by means of a discharge gun,
   wherein the container comprises a first and second chambers for accommodating the components,
   a plunger means for simultaneously discharging the components from the first and second chambers,
   a mixer for mixing the components discharged from the first and second chambers, the mixer comprising a helix and a discharge tube, wherein the helix and discharge tube are pre-installed firmly and non-displaceably on the container, and
   a sealing means for sealing the first and second chambers, the first and second chambers designed to be opened without uninstalling the mixer, and
   wherein the plunger means comprises at least one plunger rod which is assigned to a plunger and is accommodated displaceably in a guided manner in a retaining section of the container,
   which retaining section faces away from the mixer, in such a manner that the plunger rod is provided essentially flush with a front side of the retaining section, which front side faces away from the mixer, before the components are discharged,
   wherein the plunger means has a transfer tappet with a plunger rod which is guided in a displaceable manner in the retaining section, from which plunger rod a plurality of actuation sections, which are each assigned to one of the first or second chambers, project in the direction of the mixer,
   the sealing means configured in such a manner that it automatically, as a function of an internal pressure in the first and second chambers,
   frees a flow connection between the first and second chambers and the mixer when the plunger means is actuated,
   wherein each the first and second chambers comprises a discharge opening into which is inserted a sealing plunger as a sealing means,
   the sealing means designed to be completely pulled out of the discharge openings of the first and second chambers by the pressure of the components to be discharged from a first inserted position of the sealing means which seals the discharge openings of the first and second chambers to a second pulled out position of the sealing means which completely opens the discharge openings of the first and second chambers,
   wherein the first and second chambers each have a preferably channel-like discharge opening,
   which has a first region with a reduced cross-sectional area and a further region with a widened cross-sectional area, to which is assigned a sealing plunger for sealing and freeing the discharge openings of the first and second chambers,
   which plunger is designed to be displaced from the first region into the further region, as a sealing means with a contour which is matched to an inner contour of the reduced cross-sectional area of the first region,
   so that the sealing plunger, in a position displaced from the first region into the second region, frees a flow connection between the first and second chambers and the mixer.

2. Container according to claim 1
   wherein the mixer is fixed releasably to the container and/or at least one discharge opening of the chambers.

3. Container according to claim 1 wherein
the retaining section, which faces away from the mixer, has a first region with a smaller outer diameter and an adjoining second region, which faces away from the mixer, with a larger outer diameter,
with the first region being longer in an axial direction of the container than the second region.

4. Container according to claim 1 wherein
the chambers are arranged coaxially with respect to each other, with one of the chambers surrounding the other chamber in an annular manner.

5. Container according to claim 1, wherein
each actuation section is assigned to a discharge plunger which can be displaced in the respective chamber.

6. Container according to claim 1, wherein
the plunger rod and the actuation sections of the transfer tappet are configured to be integral with each other.

7. Container for storing and discharging at least two components according to claim 1,
wherein the container has in an opaque housing at least two chambers for accommodating the components,
the plunger means for simultaneously discharging the components from the chambers and
the mixer for mixing the components discharged from the chambers, which mixer is pre-installed on the container, and
wherein a window is provided in the housing, the window is configured in such a manner that a marking element, which is assigned to the plunger means, is visible through the window.

8. Container according to claim 7 comprising a scale and/or grid that is assigned to the window and/or to the marking element.

9. Container according to claim 7 wherein
the window is configured as an at least partially transparent or translucent lid and/or retaining section.

10. Container according to claim 1 wherein
the mixer is a static mixer comprising a mixing element for moving around and/or deflecting the components to be mixed and
a tube which surrounds the mixing element, with spring arms being provided, which are integral with the housing of the container, project in an axial direction towards the mixer and have radially inwardly projecting ribs with which the tube are to be locked to the housing.

11. Container according to claim 1 wherein
at least one of the discharge plungers of the plunger means comprises at least one ventilation opening for ventilating at least one of the chambers after filling.

12. Container according to claim 11 wherein
the ventilation opening is closable in a sealing manner by an actuation section of the transfer tappet.

13. Container according to claim 12, wherein the ventilation opening is closeable in a sealing manner by a front side annular projection of the actuation section.

14. A container according to claim 1 further comprising a discharge device,
wherein the discharge device comprises a receptacle at least for the retaining section of the container and
a tappet which is displacable relatively to the container, the outer diameter of which tappet is less than or equal to that of the plunger rod of the container.

15. Container according to claim 1, further comprising a common outlet channel downstream of the discharge openings of the first and second chambers.

16. Container according to claim 15, wherein the sealing means divides the common outlet channel into two channels, when the sealing means is in the second pulled out position of the sealing means.

* * * * *